United States Patent
Botea et al.

(10) Patent No.: US 11,132,621 B2
(45) Date of Patent: Sep. 28, 2021

(54) CORRECTION OF REACTION RULES DATABASES BY ACTIVE LEARNING

(71) Applicant: International Business Machines Corporation, Armonk, NY (US)

(72) Inventors: Adi I. Botea, Dublin (IE); Beat Buesser, Dublin (IE); Bei Chen, Blanchardstown (IE); Hiroshi Kajino, Tokyo (JP); Akihiro Kishimoto, Castleknock (IE)

(73) Assignee: International Business Machines Corporation, Armonk, NY (US)

( * ) Notice: Subject to any disclaimer, the term of this patent is extended or adjusted under 35 U.S.C. 154(b) by 988 days.

(21) Appl. No.: 15/813,491

(22) Filed: Nov. 15, 2017

(65) Prior Publication Data

US 2019/0147370 A1     May 16, 2019

(51) Int. Cl.
*G06N 20/00* (2019.01)
*G06F 16/23* (2019.01)
*G16C 20/90* (2019.01)
*G16C 20/10* (2019.01)
*G16C 20/70* (2019.01)

(52) U.S. Cl.
CPC ......... *G06N 20/00* (2019.01); *G06F 16/2379* (2019.01); *G16C 20/10* (2019.02); *G16C 20/90* (2019.02); *G16C 20/70* (2019.02)

(58) Field of Classification Search
CPC .... G06N 20/00; G06F 16/2379; G16C 20/10; G16C 20/90; G16C 20/70
See application file for complete search history.

(56) References Cited

U.S. PATENT DOCUMENTS

| 7,020,592 B2 | 3/2006 | Yamazaki et al. |
| 7,751,988 B2 * | 7/2010 | Kita ............... G16C 20/10 |
| | | 702/27 |
| 7,991,730 B2 * | 8/2011 | Wagner ............ G16C 20/10 |
| | | 707/712 |

(Continued)

OTHER PUBLICATIONS

Papadatos G., Davies M., Dedman N., Chambers J., Gaulton A., Siddle J., Koks R., Irvine S.A., Pettersson J., Goncharoff N.etal. . SureChEMBL: a large-scale, chemically annotated patent document database. Nucleic Acids Res. 2016; 44:D1220-D1228. (Year: 2015).*

(Continued)

*Primary Examiner* — Paulinho E Smith
(74) *Attorney, Agent, or Firm* — Kelsey M. Skodje (57) ABSTRACT

A system and method for reaction rules database correction. The method includes receiving a user-input correction to a first reaction rule in a reaction rules database, and locating a second reaction rule in the reaction rules database that is similar to the first reaction rule. The method also includes calculating a correctness score for the second reaction rule, and determining that the correctness score for the second reaction rule is below a threshold correctness score. Additionally, the method includes presenting, in response to the determining that the correctness score for the second reaction rule is below the threshold correctness score, the second reaction rule to a user, receiving a user-input correction to the second reaction rule, and updating the reaction rules database to include the user-input correction to the second reaction rule.

20 Claims, 6 Drawing Sheets

(56) References Cited

U.S. PATENT DOCUMENTS

| | | | | |
|---|---|---|---|---|
| 9,031,977 | B2* | 5/2015 | Smith | G06F 16/248 707/769 |
| 2002/0049548 | A1* | 4/2002 | Bunin | G16C 20/90 702/32 |
| 2002/0111782 | A1 | 8/2002 | Klaffke et al. | |
| 2005/0042663 | A1* | 2/2005 | Blinov | G16B 5/00 435/6.18 |
| 2005/0170379 | A1* | 8/2005 | Kita | G01N 33/6803 435/6.18 |
| 2005/0246316 | A1* | 11/2005 | Lawson | G16C 20/70 |
| 2007/0212719 | A1* | 9/2007 | Hlavacek | G16B 5/00 435/6.14 |
| 2007/0219059 | A1* | 9/2007 | Schwartz | A61B 7/003 482/8 |
| 2008/0120041 | A1 | 5/2008 | Ridder et al. | |
| 2009/0024575 | A1* | 1/2009 | Wagner | G16C 20/10 |
| 2013/0041683 | A1 | 2/2013 | Boissel | |
| 2015/0269356 | A1 | 9/2015 | Pallai et al. | |
| 2016/0115265 | A1* | 4/2016 | Scott | C07F 17/00 526/131 |
| 2016/0162632 | A1 | 6/2016 | Yun et al. | |
| 2016/0371435 | A1* | 12/2016 | Pauletto | G06F 16/2365 |
| 2018/0089582 | A1* | 3/2018 | Bouillet | G06N 20/20 |
| 2018/0096100 | A1* | 4/2018 | Alzate | G16B 40/00 |
| 2018/0101663 | A1* | 4/2018 | Botea | G16C 20/10 |
| 2018/0114140 | A1* | 4/2018 | Chen | G06F 16/9024 |
| 2018/0253453 | A1* | 9/2018 | Botea | G06F 16/217 |
| 2018/0293511 | A1* | 10/2018 | Bouillet | G06N 5/022 |
| 2018/0314978 | A1* | 11/2018 | Kajino | G06N 20/00 |
| 2018/0349514 | A1* | 12/2018 | Alzate Perez | G06F 16/24522 |
| 2019/0095515 | A1* | 3/2019 | Buesser | G06N 3/0454 |
| 2019/0147370 | A1* | 5/2019 | Botea | G06F 16/2379 706/11 |
| 2020/0050947 | A1* | 2/2020 | Kishimoto | G06F 16/90335 |
| 2020/0168302 | A1* | 5/2020 | Isayev | G06N 3/006 |

OTHER PUBLICATIONS

Smith C, Todd M, Patiny L, Swain C, Southan C, Williamson A, Clark A (2016) SCINDR—The SCience INtroDuction Robot that will Connect Open Scientists. Research Ideas and Outcomes 2,p. 1-9 (Year: 2016).*

P. Gund, E. J. J. Grabowski, D. R. Hoff, G. M. Smith, J. D. Andose, J. B. Rhodes and W. T. Wipke, J. Chem. Inf. Comput. Sci., 1980, 20, 88-93 (Year: 1980).*

Yamamoto, R., Komeno, T., and Kanehisa, M., Improvement of the LIGAND chemical database, Genome Informatics, 13: 492-493, 2002. (Year: 2002).*

Michael P. S. Brown, William Noble Grundy, David Lin, Nello Cristianini, Charles Walsh Sugnet, Terrence S. Furey, Manuel Ares, David Haussler. Proceedings of the National Academy of Sciences Jan. 2000, 97 (1) 262-267 (Year: 2000).*

Stéphanie Rialle, Liza Felicori, Camila Dias-Lopes, Sabine Pérès, Sanaâ El Atia, Alain R. Thierry, Patrick Amar, Franck Molina, BioNetCAD: design, simulation and experimental validation of synthetic biochemical networks, Bioinformatics, vol. 26, Issue 18, Sep. 15, 2010, pp. 2298-2304, (Year: 2010).*

Kher S, Peng J, Wurtele ES, Dickerson J. In: Pérez-Sánchez H, editor. Hierarchical Biological Pathway Data Integration and Mining, Bioinformatics: IntechOpen; 2012 (Year: 2012).*

Smith C, Todd M, Patiny L, Swain C, Southan C, Williamson A, Clark A (2016) SCINDR—The SCienceINtroDuction Robot that will Connect Open Scientists. Research Ideas and Outcomes 2: e9995. (Year: 2016).*

Pallara, C.; Rueda, M.; Abagyan, R.; Fernandez-Recio, J. Conformational Heterogeneity of Unbound Proteins Enhances Recognition in Protein-Protein Encounters. J. Chem. Theory Comput. 2016, 12, 3236-3249. (Year: 2016).*

G. Papadatos, Mark Davies, Nathan Dedman, Jon Chambers, Anna Gaulton, James Siddle, Richard Koks, Sean A. Irvine, Joe Pettersson, Nicko Goncharoff, Anne Hersey, John P. Overington, SureChEMBL: a large-scale, chemically annotated patent document database, Nucleic Acids Research, vol. 44, Issue D1, (Year: 2016).*

Blurock, E., "Computer-Aided Synthesis Design at RISC-Linz: Automatic Extraction and Use of Reaction Classes," Journal of Chemical Information and Modeling, (J. Chem. Inf. Comput. Sci.), 1990, vol. 30, No. 4, pp. 505-510.

Heifets et al., "Construction of New Medicines via Game Proof Search," Proceedings of the 26th AAAI Conference on Artificial Intelligence, Jul. 2012, AAAI' 12, 7 pages, AAAI Press. http://www.cs.toronto.edu/~aheifets/ChemicalPlanning/.

Kajino et al., "Active Learning for Multi-relational Data Construction," WWW '15: Proceedings of the 24th International Conference on World Wide Web, May 2015, pp. 560-569, ACM. DOI: 10.1145/2736277.2741103.

Kashima et al., "Marginalized Kernels Between Labeled Graphs," Proceedings of the Twentieth International Conference on Machine Learning (ICML—2003), 2003, 8 pages.

Kayala et al., "Learning to Predict Chemical Reactions," Author manuscript, Sep. 26, 2012, pp. 1-22. https://www.ncbi.nlm.nih.gov/pmc/articles/PMC3193800/.

Law et al., "Route Designer: A Retrosynthetic Analysis Tool Utilizing Automated Retrosynthetic Rule Generation," Journal of Chemical Information and Modeling, 2009, 49(3), pp. 593-602.

Lowe, D M., "Extraction of chemical structures and reactions from the literature," Dissertation for the degree of Doctor of Philosophy, Pembroke College, Jun. 2012, 210 pages.

Muller et al., "Models for Identification of Erroneous Atom-to-Atom Mapping of Reactions Performed by Automated Algorithms," Journal of Chemical Information and Modeling, 2012, 52(12), pp. 3116-3122 (Abstract).

Settles, B., "Active Learning Literature Survey," Computer Sciences Technical Report 1648, University of Wisconsin-Madison, Updated Jan. 26, 2010, 67 pages.

Tong et al., "Support Vector Machine Active Learning with Applications to Text Classification," Journal of Machine Learning Research, 2001, pp. 45-66.

Wilcox et al., "A Self-Organized Knowledge Base for Recall, Design, and Discovery in Organic Chemistry," Pierce and Hohne; Artificial Intelligence Applications in Chemistry ACS Symposium Series, Apr. 1986, pp. 209-230. doi: 10.1021/bk-1986-0306.ch018.

Alzate et al., "Recommending Novel Reactants to Synthesize Chemical Products," U.S. Appl. No. 15/284,612, filed Oct. 4, 2016.

Botea et al., "Efficient Retrosynthesis Analysis," U.S. Appl. No. 15/286,972, filed Oct. 6, 2016.

Botea et al., "Iterative Widening Search for Designing Chemical Compounds," U.S. Appl. No. 15/446,786, filed Mar. 1, 2017.

Mell et al., "The NIST Definition of Cloud Computing: Recommendations of the National Institute of Standards and Technology," Special Publication 800-145, Sep. 2011, 7 pages, National Institute of Standards and Technology, Gaithersburg, MD.

\* cited by examiner

CORRECTION OF REACTION RULES DATABASES BY ACTIVE LEARNING

BACKGROUND

The present disclosure relates to machine learning and more specifically to correcting databases of chemical reaction rules by active learning methods.

Chemical databases contain information about chemical compounds, reactions, thermophysical data, etc. This information can be manually input, or automatically gathered from a variety of text and/or image sources, such as chemical literature, textbooks, web pages, etc. Chemical databases are used for a number of purposes. For example, these databases can be used to search for topics in scientific literature or chemical structures and substructures. Chemical databases can also be used to predict the products of theoretical reactions, generate theoretical structures, retrosynthetically design syntheses of target compounds, predict the properties of compounds, etc.

SUMMARY

Various embodiments are directed to a method of reaction rule database correction. The reaction rules database can include reaction rules extracted from sources such as scientific articles, books, and patents. The method can include receiving a first user-input correction to a first reaction rule in a reaction rules database, locating a second reaction rule in the reaction rules database that is similar to the first reaction rule, and calculating a correctness score for the second reaction rule, wherein the correctness score is a measure of how similar the second reaction rule is to the first reaction rule. The method can also include determining that the correctness score for the second reaction rule is below a threshold correctness score, and in response to the determining that the correctness score for the second reaction rule is below the threshold correctness score, presenting the second reaction rule to a user. Further, the method can include receiving a second user-input correction to the second reaction rule, and updating the reaction rules database to include the second user-input correction to the second reaction rule. In some embodiments, the first reaction rule and the second reaction rule have incorrect bonds. Presenting the second reaction rule to the user can include automatically opening a new window of a computer-assisted synthetic design program user interface. Additionally, an alert can be generated when the correctness score for the second reaction rule is below the threshold correctness score.

The method can also include locating an additional reaction rule that is similar to the second reaction rule, calculating a correctness score for the additional reaction rule, determining that the correctness score for the additional reaction rule is below the threshold correctness score, and in response to determining that the correctness score for the additional reaction rule is below the threshold correctness score, presenting the additional reaction rule to the user. The method can also include receiving a user-input correction to the additional reaction rule, and updating the reaction rules database to include the user-input correction to the additional reaction rule. Further, the method can include receiving a user-input confidence level for the user-input correction to the second reaction rule, determining that the confidence level is below a threshold confidence level, and in response to determining that the confidence level is below the threshold confidence level, presenting the second reaction rule to a second user. Upon receiving confirmation of the second reaction rule from the second user, the reaction rules database can be updated to include the confirmation.

DETAILED DESCRIPTION

Chemical databases are used to store chemical information, and to supplement the knowledge and strategies of scientists and engineers. These databases contain information relating to categories such as chemical compounds, chemical reactions, reaction rules, thermophysical data etc. This information is gathered from a variety of text and/or image sources, such as chemical literature, patents, textbooks, web pages, etc. This information can be manually input or automatically populated based on the gathered information. One example of a chemical database is the Beilstein database, which stores experimentally verified information about chemical reactions and substances found in scientific literature ranging from 1771 to the present day. The Beilstein database began as a handbook of organic chemistry in 1881, but was later converted into an electronic database. Today, there are a number of literature databases that contain structures and other chemical information from scientific articles, supplementary materials, and patents (e.g., Reaxys by Elsevier, Scopus by Elsevier, ChemSpider by the Royal Society of Chemistry, SciFinder by Chemical Abstract Service (CAS), Science and Technical Information Network (STN International) by CAS, etc.).

Additional examples of chemical databases can include crystallographic databases, such as the Crystallography Open Database (COD), the Research Collaboratory for Structural Bioinformatics' Protein Data Bank (RCSB PDB), the Open Access Crystal Morphology Database (CMD), etc. These databases store crystal structures of and/or morphological information about minerals, metals and alloys, organic compounds, nucleic acids, biological macromolecules, polymers, organometallic compounds, etc. Crystallographic databases are typically relational databases, and can be searched by keywords, physical properties, chemical elements, partial structures, morphology, compound names, lattice parameters, etc. Additional examples of databases that contain molecular structure information can include the National Institute of Health PubChem, commercial databases such as eMolecules and The ChemExper Chemical Directory by ChemExper, the New York University Library of 3-D Molecular Structures, the Environmental Protection Agency's Distributed Structure-Searchable Toxicity (DSSTox) Database Network, etc.

Databases that store thermodynamic and thermophysical data are another category of chemical databases. For example, the Dortmund Data Bank (DDB) stores experimental data collected from more than 92,000 scientific articles, books, private communications, company reports, patents, theses, conference presentations, etc. Additional examples of chemical databases can include nuclear magnetic resonance (NMR) spectra databases, reaction databases, reaction rules databases, etc. Reaction rules databases store reaction rules (e.g., fundamental steps in a chemical reaction), which are based on information such as that stored in the aforementioned chemical databases. This is discussed in greater detail below.

The information collected in chemical databases is extensive. For example, the literature database Reaxys has, as of October 2016, more than 105 million chemical compounds, 45 million chemical reactions, and 500 million experimental facts. This information is gleaned from over 16,000 chemistry-related periodicals, patents from all major world patent offices, and approximately 450 scientific journals and textbooks published since 1771. The data stored in chemical databases can be used in a variety of applications other than providing searchable knowledge to users. For example, the databases can provide data used to predict the outcome of a reaction when a user enters starting materials and/or reaction conditions. Information from these databases can also be used to predict properties of compounds based on their structures. For example, a user can enter a structure of an existing or theoretical compound into a prediction program. The program then determines the likely properties of the compound based on fundamental principles and/or experimental information about similar structures and materials.

Another application of chemical database information is in retrosynthetic analysis. Retrosynthetic analysis is a method of determining possible synthetic paths to a target compound. In the past, this strategy relied solely on the background knowledge and reasoning skills of human scientists. For example, a scientist attempting to design a new drug may decide that adding a hydroxyl functional group to the structure of an existing drug that is an organic compound could provide beneficial new properties. The scientist might approach this by considering reactions that can add hydroxyl groups to organic compounds. The scientist could then narrow these reactions down to known reactions involving organic compounds with structures similar to the existing drug. The reaction parameters could be narrowed still further by considering practicalities such as availability and/or safety of starting materials and solvents, reaction time, reaction yield, difficulty of techniques, access to equipment, number of synthetic steps, etc.

However, even with the amount of information available to the modern scientist through chemical databases, this approach to synthesizing a new drug is impractical. Designing a new drug takes an average of 12 years and $800 million per drug. Additionally, the number of theoretical candidates for a single drug can range from 5,000-10,000 compounds, with approximately 250 compounds showing promise. The time, effort, and materials required to test all of these compounds result in a significant portion of the cost of developing a new drug. Further, even when a candidate compound is selected to enter the clinical phase, the chance that it will receive approval from the Food and Drug Administration (FDA) is about one in ten. Therefore, strategies that increase the efficiency of drug design and discovery are of interest today. One strategy that can be employed is computer-assisted synthesis design (CASD), which employs retrosynthetic analysis carried out using machine learning techniques.

Retrosynthetic analysis carried out using machine learning combined with the information available in chemical databases offers an important tool for modern chemical synthesis. A target compound is entered into a CASD program, which then uses machine learning techniques to quickly determine possible synthetic pathways to a new compound from chemical database information and, in particular, chemical reaction rules databases. Reaction rules are a type of abstracted chemical reaction, and are discussed in greater detail below. Using machine learning techniques allows a large number of candidate compounds to be synthesized and tested, speeding the process of drug discovery considerably. Further, it should be noted that retrosynthetic analysis can aid in uncovering synthetic approaches to forming compounds other than drugs. Examples of these compounds can include polymers, polymer additives, catalysts, pesticides, dyes, artificial flavorings and sweeteners, compounds used in fundamental research, peptidomimetics, synthetic proteins, nanostructures, artificial genes, etc.

In the past, CASD programs relied upon manually input chemical information and reaction rules. Therefore, retrosynthetic analysis was limited by the pace and knowledge of humans. However, reaction rules can now be extracted by automatic methods. This extraction employs natural language processing and image processing to extract reaction examples (i.e., known compound syntheses) from sources such as those discussed above with respect to various chemical databases. The known reactions are generalized into reaction rules by first identifying reaction cores of the compound substructures. This is carried out using atom-to-atom mapping between reactants and products in an example reaction. The reaction core consists of substructures that have mapped atoms with the same attributes in both the reactants and products. The reaction core is then extended to include relevant neighboring functional groups. Then, similar reaction cores from different example reactions are grouped together, and combined to form generalized reaction cores. A reaction rule is then completed. The reaction rule represents the generalized reaction core with ranges for each generalized property across the example reactions.

This reaction rule extraction method provides vast numbers of reaction rules that are stored in reaction rules databases, and can be used to retrosynthetically generate possible pathways to target compounds. However, automatic reaction rule extraction results in a significant number of errors, particularly when the number of example reactions is inadequate for forming a reliable generalized core. Corrections can be made by human users, but the great number of reaction rules makes it extremely difficult for human users to efficiently locate the errors. Therefore, updates to reaction rules databases to correct errors in reaction rules cannot rely solely on human error detection. A method for improving the efficiency of reaction rule correction by active learning techniques is disclosed herein. Active learning is a type of semi-supervised machine learning in which a learning algorithm interactively queries a user by requesting labels for selected data. This is discussed in greater detail below.

Figure 1:
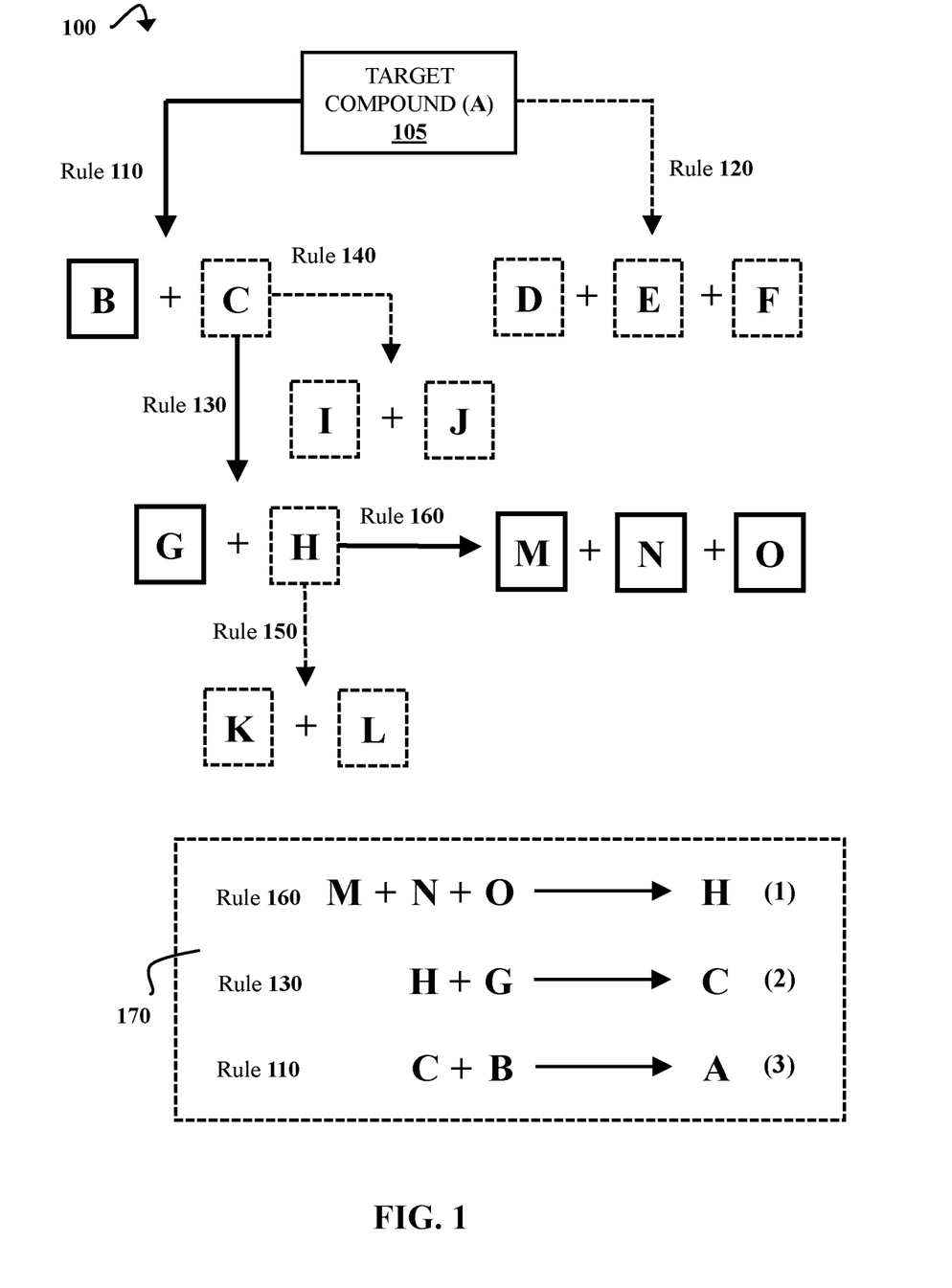
FIG. 1 is a schematic diagram illustrating a generic example of retrosynthetic analysis, according to some embodiments of the present disclosure.

FIG. 1 is a schematic diagram illustrating a generic example of retrosynthetic analysis. A target compound 105 is entered into a CASD program. The target compound 105 is entered as a compound name, a chemical structure, and/or a molecular fingerprint for identifying a target compound. Examples of computer-readable formats in which a chemical structure of the target compound 105 can be entered can include Chemical Markup Language (CML), SYBYL line notation (SLN), simplified molecular-input line-entry system (SMILES) notation, Ghemical format, Crystallographic Image File (CIF) format, Protein Data Bank (PDB) file format, XYZ file format, density functional theory (DFT) calculation, etc. The molecular fingerprint of the target compound 105 is represented by bit strings that summarize molecular information, such as combinatorial features or information about functional groups.

The CASD program locates compounds with known synthesis pathways that are similar to the target compound 105. For example, similar compounds can be located based on Jaccard similarity, descriptive network properties and graph theory, chemical semantic measures, autocorrelation polarizability, etc. In some embodiments, techniques for filtering the similarity search results can be used, such as succinct multibit tree searching or succinct interval splitting tree algorithm searching.

The CASD program then locates a reaction rule for synthesizing each compound in the set of similar compounds, and applies the reaction rule to the target compound 105 in order to generate precursors. The program also determines whether the precursors are starting materials (e.g., compounds that are commercially available or have commonly known syntheses). If a precursor is not a starting material, the process is repeated to find reaction rules for synthesizing the precursor. The synthetic pathway to the target compound 105 is considered complete when all precursors are starting materials.

In process 100, two reaction rules, Rule 110 and Rule 120, that represent synthetic pathways to the target compound A 105 are found. Rule 110 is a reaction between compound B and compound C. Compound B is illustrated in a box with a bold line to indicate that it is a starting material, and compound C is illustrated in a box with a dashed line to indicate that it must be synthesized. Rule 120 is a reaction to form the target compound 105 from compounds D, E, and F, each of which must be synthesized. The synthetic pathway that uses Rule 110 is selected as the simplest path because compound B is a starting material.

However, a synthetic path to compound C must then be determined. Again, two reaction rules are found. Rule 130 is a reaction to form compound C from compounds G and H, and Rule 140 is a reaction to form compound C from compounds I and J. Of these, only compound G is a starting material. Therefore, Rule 130 is applied, and two reaction rules for a synthetic pathway to compound H are found. Rule 150 is a reaction between two compounds that must be synthesized, compounds K and L, and Rule 160 is a reaction between three starting materials, compounds M, N, and O. Rule 160 is applied because it begins with starting materials. Therefore, a generalized synthetic pathway 170 to the target compound 105 can be constructed from Rules 110, 130, and 160.

It should be noted that the example illustrated in FIG. 1 is a simplified example, and that the number of reaction rules located in a database for one compound can be extremely large (e.g., hundreds, thousands, tens of thousands, etc.). Further, factors other than the quickest path to a commercially available compound are often taken into consideration. For example, Rule 130 was chosen in this example because it leads directly to a starting material (compound B). Rules for generating compounds I and J from Rule 140 are not shown. However, it could be that compounds I and J have facile syntheses, and that compound G is commercially available, but prohibitively expensive. In a case such as this, continuing the path begun in Rule 140 may be more practical than that of Rule 130, despite requiring additional steps. Variations in reaction parameters are discussed in greater detail above.

Figure 2:
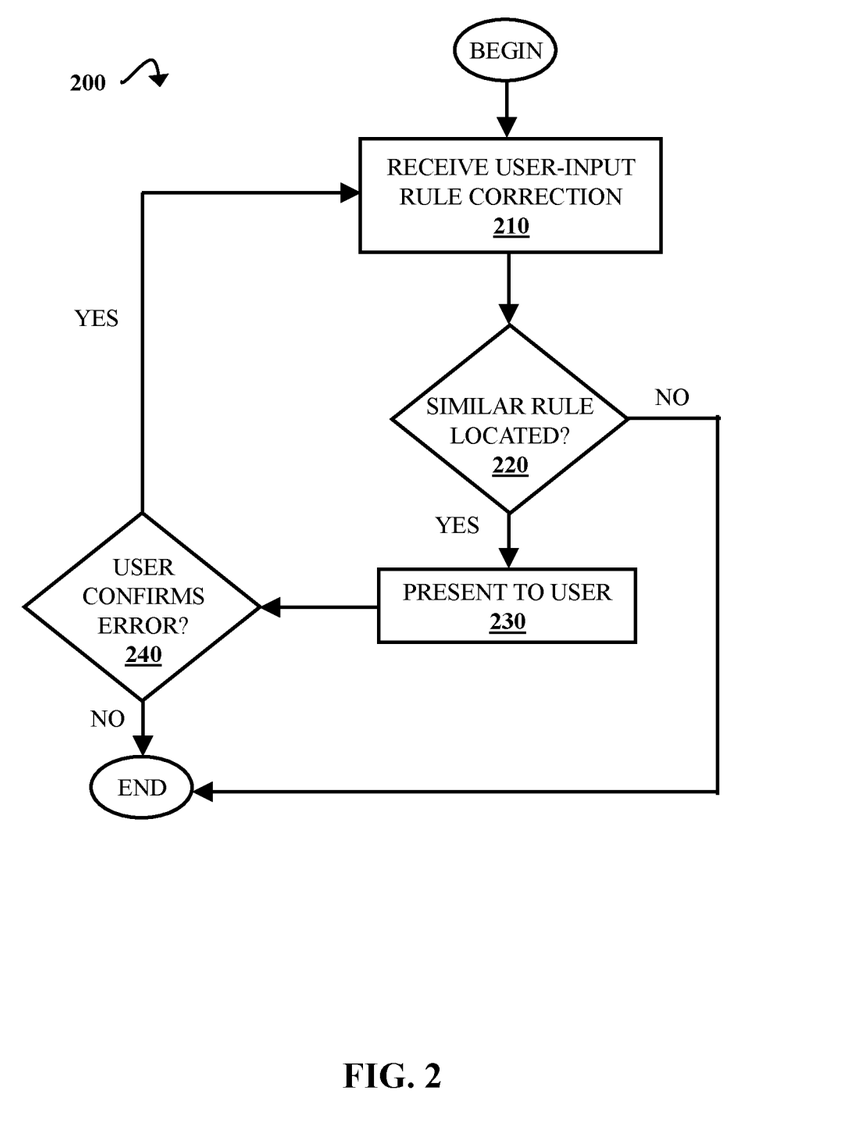
FIG. 2 is a flow diagram illustrating a process of correcting a reaction rules database, according to some embodiments of the present disclosure.

FIG. 2 is a flow diagram illustrating a process 200 of correcting a reaction rules database. The process begins when at least one user-input reaction rule correction is received. This is illustrated at step 210. A user locates at least one reaction rule error while using a CASD program. Examples of reaction rule errors can include incorrect atoms, incorrect bonds, incorrect stereochemistry, etc. Further, reaction rules can include information about reaction temperatures, toxicity of compounds, reaction yields, reaction speed, etc., and a user may encounter mistakes in this information as well. Based on the user's knowledge of reaction rules, the user inputs a corrected reaction rule, and the corrected rule is stored in the reaction rules database. However, in some embodiments the user can flag an error without entering a corrected rule. Additionally, the user can delete an incorrect reaction rule without entering a corrected rule. Herein, any update to a potentially incorrect reaction rule entered by a user is referred to as a correction (e.g., entering a corrected rule, deleting an incorrect rule, editing a rule, assigning a confidence level marking, flagging an error, etc.).

Once the user-input rule correction has been received, a similarity search is carried out to determine whether there are reaction rules in the database that are similar to the corrected rule. This is illustrated at step 220. If a reaction rule in the database is similar to the rule that the user corrected, it is possible that the located similar rule is incorrect as well. The similarities of the reaction rules are represented by correctness scores. A high correctness score indicates low similarity between a reaction rule in the database and the corrected reaction rule. Reaction rules with correctness scores below a threshold correctness score are considered to have substantial similarity to the corrected reaction rules, and thus are flagged as potential errors.

The threshold correctness score can be preset or entered by a user. In some embodiments the threshold correctness score can be adjusted by the user in order to raise or lower the number of presented potential errors. There can be more than one level of threshold correctness score (e.g., a low threshold and a high threshold), which can indicate different levels of probability of a rule being incorrect.

If no potential errors (i.e., reaction rules with correctness scores below the threshold correctness score) are located, the process ends. However, if one or more potential errors are located, the potential errors are presented to the user. This is illustrated at step 230. In some embodiments, potential errors are displayed to the user according to their correctness score (e.g., from lowest to highest correctness score). Additionally, the similar rules can be automatically displayed on a CASD program user interface while the user operates the CASD program. For example, a new window displaying the potential errors can automatically open once the similar rules have been located. However, the similar reaction rules can also be stored, and accessed by opening a new window or clicking on a link that will take the user to a display of the potential errors. Additionally, in some embodiments an alert can be triggered when potential errors are located. Examples of alerts can include sounds, pop-up messages, emails, short message service ('SMS' or text) messages, flashing lights, force or haptic feedback, electric impulses, etc.

The potential errors are reviewed by a user who specifies whether these rules are in fact errors. This is illustrated at step 240. The reaction rules can be classified as either true or false. If the user indicates that the potential error is a valid reaction rule (i.e., true), the process ends. However, if the user determines that a displayed reaction rule is incorrect (i.e., false), the user confirms the error and enters a correction. The process then returns to step 210 with the newly entered correction.

In some embodiments, the user assigns a confidence level to a reaction rule. For example, a user may be unsure whether a reaction rule presented as a potential error is correct. If so, the user can mark the rule as incorrect with a high, medium, or low confidence level. It should also be noted that there can be more than three levels, and that the levels can be expressed in a variety of ways (e.g., words, letters, percentages, numbers on a scale, colors, icons, etc.). The user can also attach a confidence level to a correction. The confidence level can be used to adjust the search rankings of the reaction rules. Additionally, if a user indicates less than complete confidence in a reaction rule (e.g., a confidence level below a confidence level threshold), another user could be asked for a second confirmation. If the second user confirms that the rule is incorrect, the reaction rules database is updated to increase the confidence level. Further, the second user can also enter a confidence level in some embodiments.

Figure 3:
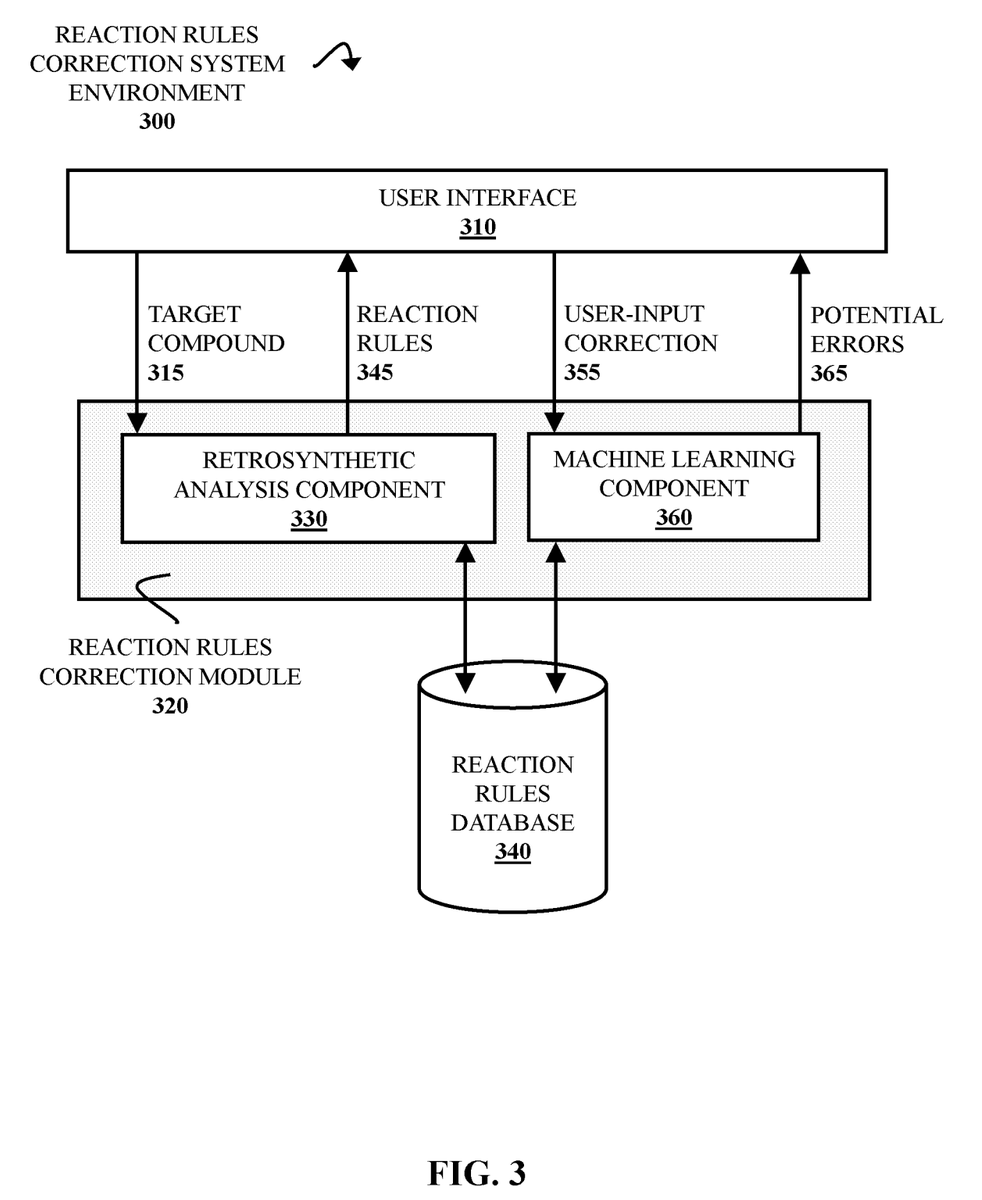
FIG. 3 is a block diagram illustrating a reaction rules correction system environment, according to some embodiments of the present disclosure.

FIG. 3 is a block diagram illustrating a reaction rules correction environment 300. A user enters a target compound 315 into a reaction rules correction module 320 via a user interface 310. The target compound 315 is entered as a compound name, a chemical structure, and/or a molecular fingerprint for identifying a target compound. The target compound 315 is received by a retrosynthetic analysis component 330. The retrosynthetic analysis component 330 searches a reaction rules database 340, and locates reaction rules 345 that provide potential synthetic pathways to the target compound 315. The process of carrying out retrosynthetic analysis on a target compound is discussed in greater detail with respect to FIG. 1.

The reaction rules 345 are presented to the user via the user interface 310. If the user identifies an error in a reaction rule 345, the user enters a correction 355 (e.g., marks the rule "false"). Corrections are discussed in greater detail with respect to FIG. 2. The user-input correction 355 is received by a machine learning component 360 in the reaction rules correction module 320. The machine learning component 360 locates one or more reaction rules within the reaction rules database 340 that are similar to the reaction rule that was marked false by the user. These reaction rules are given correctness scores based on their similarity to the user-corrected reaction rule, and it is determined whether the rules have correctness scores below a threshold correctness score.

Reaction rules with correctness scores below the threshold correctness score (i.e., rules that may contain errors) are referred to as potential errors 365, and are displayed to the user via the user interface 310. The user confirms whether the potential errors 365 are incorrect, and enters another user-input correction 355. If the potential errors 365 are confirmed to be incorrect by the user, the machine learning component 360 updates the reaction rules database 340 to include the user-input correction 355. Examples of active learning techniques the machine learning component 360 can employ to carry out database corrections can include support vector machine (SVM) algorithms, graph-based active learning methods, generative adversarial active learning methods, active multi-relational learning algorithms, etc. The machine learning component 360 uses the user-input corrections 355 to learn functions for predicting the correctness of additional reaction rules.

Figure 4:
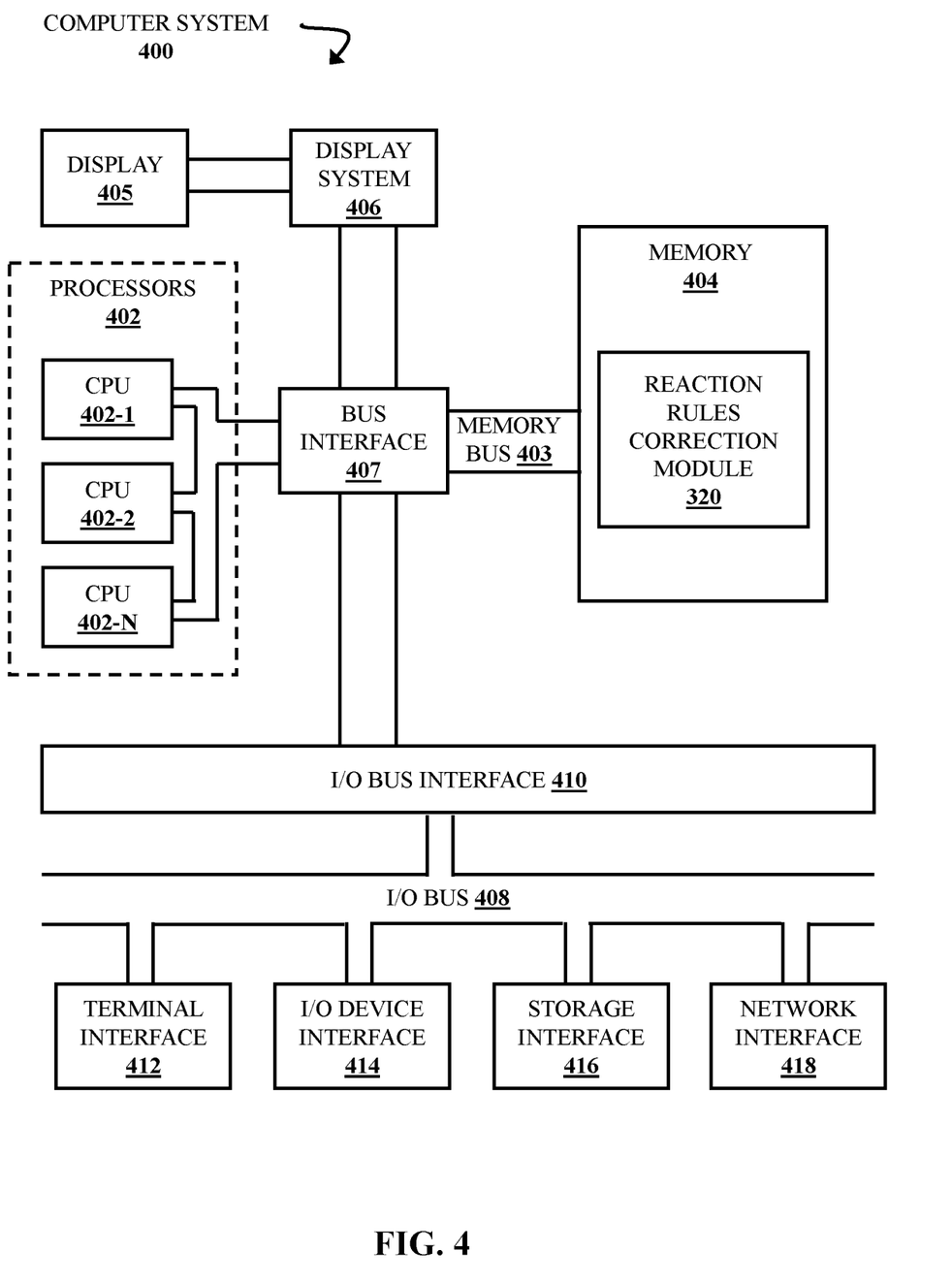
FIG. 4 is a block diagram illustrating a computer system, according to some embodiments of the present disclosure.

FIG. 4 is a high-level block diagram illustrating an exemplary computer system 400 that can be used in implementing one or more of the methods, tools, components, and any related functions described herein (e.g., using one or more processor circuits or computer processors of the computer). In some embodiments, the major components of the computer system 400 comprise one or more processors 402, a memory subsystem 404, a terminal interface 412, a storage interface 416, an input/output device interface 414, and a network interface 418, all of which can be communicatively coupled, directly or indirectly, for inter-component communication via a memory bus 403, an input/output bus 408, bus interface unit 407, and an input/output bus interface unit 410.

The computer system 400 contains one or more general-purpose programmable central processing units (CPUs) 402-1, 402-2, and 402-N, herein collectively referred to as the CPU 402. In some embodiments, the computer system 400 contains multiple processors typical of a relatively large system; however, in other embodiments the computer system 400 can alternatively be a single CPU system. Each CPU 402 may execute instructions stored in the memory subsystem 410 and can include one or more levels of on-board cache.

The memory 404 can include a random-access semiconductor memory, storage device, or storage medium (either volatile or non-volatile) for storing or encoding data and programs. In some embodiments, the memory 404 represents the entire virtual memory of the computer system 400, and may also include the virtual memory of other computer systems coupled to the computer system 400 or connected via a network. The memory 404 is conceptually a single monolithic entity, but in other embodiments the memory 404 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory can be further distributed and associated with different CPUs or sets of CPUs, as is known in any of various so-called non-uniform memory access (NUMA) computer architectures. The memory 404 also contains a reaction rules correction module 320, which is discussed in greater detail with respect to FIG. 3.

These components are illustrated as being included within the memory 404 in the computer system 400. However, in other embodiments, some or all of these components may be on different computer systems and may be accessed remotely, e.g., via a network. The computer system 400 may use virtual addressing mechanisms that allow the programs of the computer system 400 to behave as if they only have access to a large, single storage entity instead of access to multiple, smaller storage entities. Thus, though storage management system 120 is illustrated as being included within the memory 404, components of the memory 404 are not necessarily all completely contained in the same storage device at the same time. Further, although these components are illustrated as being separate entities, in other embodiments some of these components, portions of some of these components, or all of these components may be packaged together.

In an embodiment, the reaction rules correction module 320 includes instructions that execute on the processor 402 or instructions that are interpreted by instructions that execute on the processor 402 to carry out the functions as further described in this disclosure. In another embodiment, the reaction rules correction module 320 is implemented in hardware via semiconductor devices, chips, logical gates, circuits, circuit cards, and/or other physical hardware devices in lieu of, or in addition to, a processor-based system. In another embodiment, the reaction rules correction module 320 includes data in addition to instructions.

Although the memory bus 403 is shown in FIG. 4 as a single bus structure providing a direct communication path among the CPUs 402, the memory subsystem 410, the display system 406, the bus interface 407, and the input/output bus interface 410, the memory bus 403 can, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the input/output bus interface 410 and the input/output bus 408 are shown as single respective units, the computer system 400 may, in some embodiments, contain multiple input/output bus interface units 410, multiple input/output buses 408, or both. Further, while multiple input/output interface units are shown, which separate the input/output bus 408 from various communications paths running to the various input/output devices, in other embodiments some or all of the input/output devices may be connected directly to one or more system input/output buses.

The computer system 400 may include a bus interface unit 407 to handle communications among the processor 402, the memory 404, a display system 406, and the input/output bus interface unit 410. The input/output bus interface unit 410 may be coupled with the input/output bus 408 for transferring data to and from the various input/output units. The input/output bus interface unit 410 communicates with multiple input/output interface units 412, 414, 416, and 418, which are also known as input/output processors (IOPs) or input/output adapters (IOAs), through the input/output bus 408. The display system 406 may include a display controller. The display controller may provide visual, audio, or both types of data to a display device 405. The display system 406 may be coupled with a display device 405, such as a standalone display screen, computer monitor, television, or a tablet or handheld device display. In alternate embodiments, one or more of the functions provided by the display system 406 may be on board a processor 402 integrated circuit. In addition, one or more of the functions provided by the bus interface unit 407 may be on board a processor 402 integrated circuit.

In some embodiments, the computer system 400 is a multi-user mainframe computer system, a single-user system, or a server computer or similar device that has little or no direct user interface, but receives requests from other computer systems (clients). Further, in some embodiments, the computer system 400 is implemented as a desktop computer, portable computer, laptop or notebook computer, tablet computer, pocket computer, telephone, smart phone, network switches or routers, or any other appropriate type of electronic device.

It is noted that FIG. 4 is intended to depict the representative major components of an exemplary computer system 400. In some embodiments, however, individual components may have greater or lesser complexity than as represented in FIG. 4, Components other than or in addition to those shown in FIG. 4 may be present, and the number, type, and configuration of such components may vary.

In some embodiments, the data storage and retrieval processes described herein could be implemented in a cloud computing environment, which is described below with respect to FIGS. 5 and 6. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
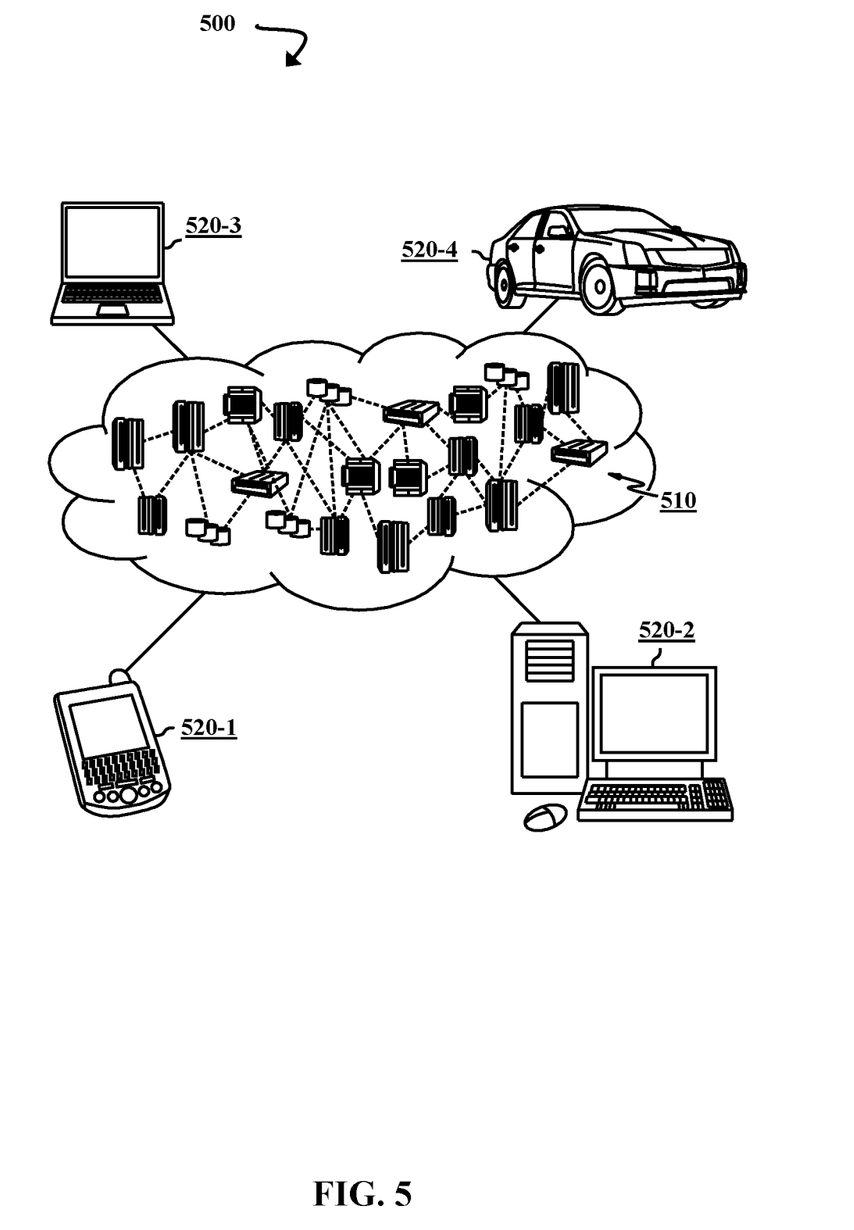
FIG. 5 is a block diagram illustrating a cloud computing environment, according to some embodiments of the disclosure

Referring now to FIG. 5, illustrative cloud computing environment 500 is depicted. As shown, cloud computing environment 500 includes one or more cloud computing nodes 510 with which local computing devices used by cloud consumers, such as, for example, personal digital assistant (PDA) or cellular telephone 520-1, desktop computer 520-2, laptop computer 520-3, and/or automobile computer system 520-4 may communicate. Nodes 510 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 520-1-520-4 shown in FIG. 5 are intended to be illustrative only and that computing nodes 510 and cloud computing environment 500 can communicate with any type of computerized device over any type of network and/or network addressable connection (e.g., using a web browser).

Figure 6:
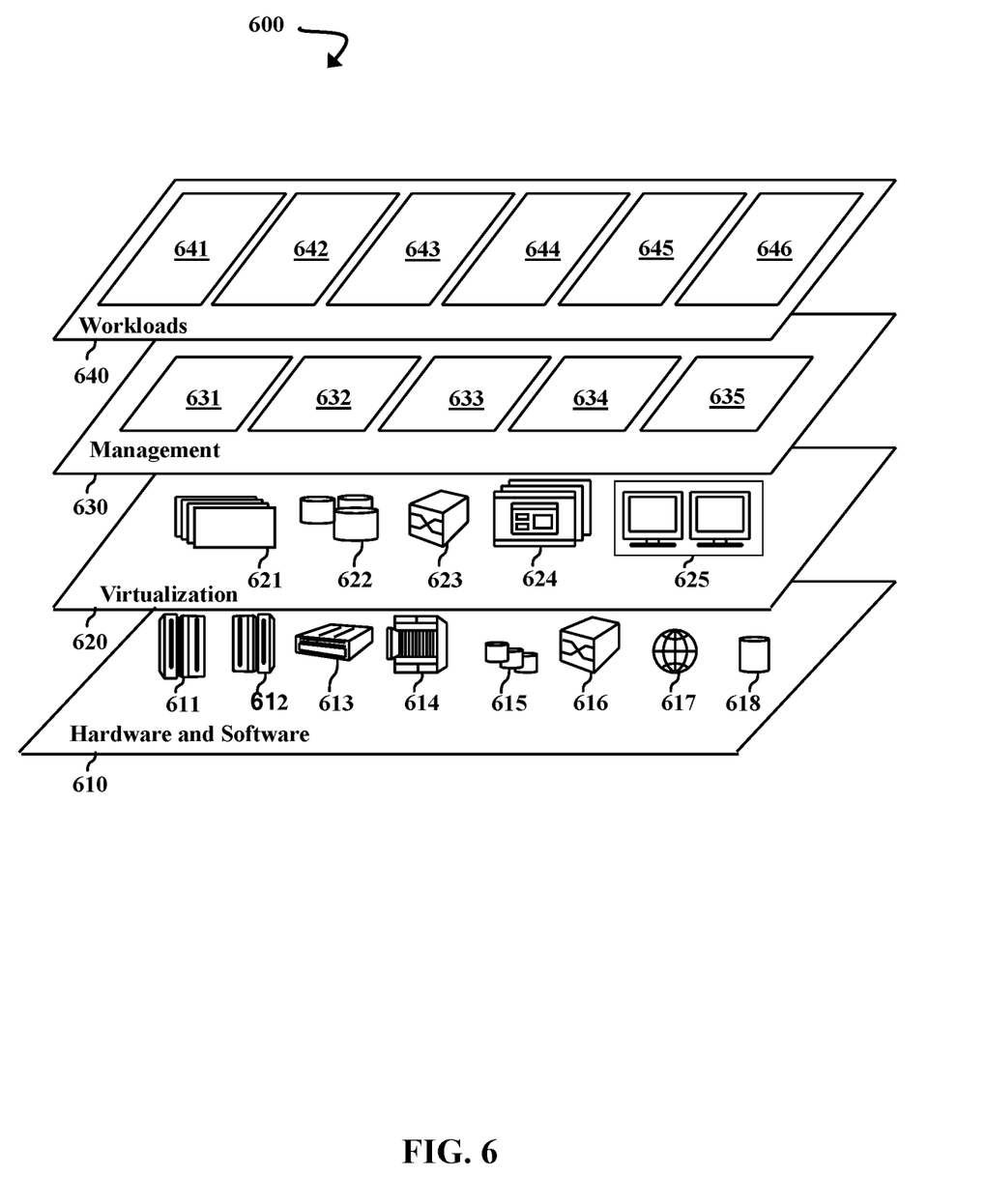
FIG. 6 is a block diagram illustrating abstraction model layers, according to some embodiments of the disclosure.

Referring now to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 610 includes hardware and software components. Examples of hardware components include: mainframes 611; RISC (Reduced Instruction Set Computer) architecture based servers 612; servers 613; blade servers 614; storage devices 615; and networks and networking components 616. In some embodiments, software components include network application server software 617 and database software 618.

Virtualization layer 620 provides an abstraction layer from which the following examples of virtual entities may be provided: virtual servers 621; virtual storage 622; virtual networks 623, including virtual private networks; virtual applications and operating systems 624; and virtual clients 625.

In one example, management layer 630 provides the functions described below. Resource provisioning 631 provides dynamic procurement of computing resources and other resources that are utilized to perform tasks within the cloud computing environment. Metering and Pricing 632 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 633 provides access to the cloud computing environment for consumers and system administrators. Service level management 634 provides cloud computing resource allocation and management such that required service levels are met. Service Level Agreement (SLA) planning and fulfillment 635 provide pre-arrangement for, and procurement of, cloud computing resources for which a future requirement is anticipated in accordance with an SLA.

Workloads layer 640 provides examples of functionality for which the cloud computing environment can be utilized. Examples of workloads and functions that can be provided from this layer include: mapping and navigation 641; software development and lifecycle management 642; virtual classroom education delivery 643; data analytics processing 644; transaction processing 645; and machine learning for reaction rule database correction 646.

The present disclosure may be a system, a method, and/or a computer program product. The computer program product may include a computer readable storage medium (or media) having computer readable program instructions thereon for causing a processor to carry out aspects of the present disclosure.

The computer readable storage medium is a tangible device that can retain and store instructions for use by an instruction execution device. Examples of computer readable storage media can include an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a component, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A method of reaction rules database correction, comprising:
 receiving a first user-input correction to a first reaction rule in a reaction rules database;
 locating a second reaction rule in the reaction rules database that is similar to the first reaction rule;
 calculating a correctness score for the located second reaction rule;
 determining that the correctness score for the located second reaction rule is below a threshold correctness score;
 presenting, in response to the determining that the correctness score for the located second reaction rule is below the threshold correctness score, the located second reaction rule to a user;

receiving a second user-input correction to the located second reaction rule;
updating the reaction rules database to include the second user-input correction and
learning, based on the updating, a function for predicting correctness scores for additional reaction rules in the reaction rules database.

2. The method of claim 1, further comprising:
locating an additional reaction rule in the reaction rules database that is similar to the located second reaction rule;
calculating a correctness score for the additional reaction rule;
determining that the correctness score for the additional reaction rule is below the threshold correctness score;
presenting, in response to the determining that the correctness score for the additional reaction rule is below the threshold correctness score, the additional reaction rule to the user;
receiving a user-input correction to the additional reaction rule; and
updating the reaction rules database to include the user-input correction to the additional reaction rule.

3. The method of claim 1, further comprising:
receiving a user-input confidence level for the second user-input correction;
determining that the user-input confidence level is below a threshold confidence level;
presenting, in response to the determining that the user-input confidence level is below the threshold confidence level, the located second reaction rule to a second user;
receiving a response from the second user confirming the second user-input correction; and
updating the reaction rules database to include the confirmation from the second user.

4. The method of claim 1, wherein the presenting the located second reaction rule includes automatically opening a new window in a user interface of a computer-assisted synthetic design program.

5. The method of claim 1, further comprising generating an alert upon determining that the correctness score for the located second reaction rule is below the threshold correctness score.

6. The method of claim 1, wherein the first reaction rule and the located second reaction rule include incorrect bonds.

7. The method of claim 1, wherein the correctness score is a measure of how similar the located second reaction rule is to the first reaction rule.

8. The method of claim 1, wherein the reaction rules database includes reaction rules extracted from at least one source selected from a group consisting of at least one scientific article, at least one book, and at least one patent.

9. A system, comprising:
at least one processing component;
at least one memory component;
a user interface;
a reaction rules database; and
a reaction rules correction module, comprising:
a machine learning component, executing on the at least one processing component, configured to:
receive a first user-input correction to a first reaction rule in the reaction rules database;
locate a second reaction rule in the reaction rules database that is similar to the first reaction rule;
calculate a correctness score for the located second reaction rule;
determine that the correctness score for the located second reaction rule is below a threshold correctness score;
present, in response to the correctness score being below the threshold correctness score, the located second reaction rule to a user, wherein the located second reaction rule is displayed on the user interface;
receive a second user-input correction to the located second reaction rule;
update the reaction rules database to include the second user-input correction to the located second reaction rule; and
based on the update, learn a function for predicting correctness scores for additional reaction rules in the reaction rules database.

10. The system of claim 9, wherein the machine learning component is further configured to:
receive a user-input confidence level for the second user-input correction;
determine that the user-input confidence level is below a threshold confidence level;
present, in response to the user-input confidence level being below the threshold confidence level, the located second reaction rule to a second user;
receive a response from the second user confirming the second user-input correction; and
update the reaction rules database to include the confirmation from the second user.

11. The system of claim 9, wherein the machine learning component is further configured to generate an alert upon determining that the correctness score for the located second reaction rule being below the threshold correctness score.

12. The system of claim 9, wherein the reaction rules correction module further comprises a retrosynthetic analysis component.

13. The system of claim 9, wherein the first reaction rule and the located second reaction rule include incorrect bonds.

14. The system of claim 9, wherein the correctness score for the located second reaction rule is a measure of how similar the located second reaction rule is to the first reaction rule.

15. A computer program product for data storage management, the computer program product comprising a computer readable storage medium having program instructions embodied therewith, the program instructions executable by a processor to cause the device to perform a method, the method comprising:
receiving a first user-input correction to a first reaction rule in a reaction rules database;
locating a second reaction rule in the reaction rules database that is similar to the first reaction rule;
calculating a correctness score for the located second reaction rule;
determining that the correctness score for the located second reaction rule is below a threshold correctness score;
presenting, in response to the determining that the correctness score for the located second reaction rule is below a threshold correctness score, the located second reaction rule to a user;
receiving a second user-input correction to the second reaction rule;
updating the reaction rules database to include the second user-input correction to the located second reaction rule; and learning, based on the updating, a function for predicting correctness scores for additional reaction rules in the reaction rules database.

16. The computer program product of claim 15, further comprising:

locating an additional reaction rule in the reaction rules database that is similar to the located second reaction rule;

calculating a correctness score for the additional reaction rule;

determining that the correctness score for the additional reaction rule is below the threshold correctness score;

presenting, in response to the determining that the correctness score for the additional reaction rule is below the threshold correctness score, the additional reaction rule to the user;

receiving a user-input correction to the additional reaction rule; and updating the reaction rules database to include the user-input correction to the additional reaction rule.

17. The computer program product of claim 15, further comprising:

receiving a user-input confidence level for the located second user-input correction;

determining that the user-input confidence level is below a threshold confidence level;

presenting, in response to the determining that the user-input confidence level is below the threshold confidence level, the located second reaction rule to a second user;

receiving a response from the second user confirming the second user-input correction; and updating the reaction rules database to include the confirmation from the second user.

18. The computer program product of claim 15, wherein the presenting the located second reaction rule includes automatically opening a new window in a user interface of a computer-assisted synthetic design program user interface.

19. The computer program product of claim 15, further comprising generating an alert upon determining that the correctness score is below the threshold correctness score.

20. The computer program product of claim 15, wherein the first reaction rule and the located second reaction rule include incorrect bonds.

* * * * *